United States Patent [19]

Oetiker et al.

[11] Patent Number: 4,547,725

[45] Date of Patent: Oct. 15, 1985

[54] METHOD AND APPARATUS FOR THE CONTINUOUS DETERMINATION OF MOISTURE POURABLE FOOD

[75] Inventors: Hans Oetiker, St. Gallen; Emanuel Kummer, Gossau, both of Switzerland

[73] Assignee: Gebruder Buhler AG, Switzerland

[21] Appl. No.: 355,596

[22] PCT Filed: Dec. 5, 1980

[86] PCT No.: PCT/CH80/00150

§ 371 Date: Feb. 17, 1982

§ 102(e) Date: Feb. 17, 1982

[30] Foreign Application Priority Data

Jun. 30, 1980 [DE] Fed. Rep. of Germany ....... 3024794

[51] Int. Cl.[4] ............................................. G01R 27/02
[52] U.S. Cl. .................................. 324/61 R; 324/61 P
[58] Field of Search ............ 426/231; 324/61 R, 61 P, 324/60 CD; 222/64; 73/74, 304 C

[56] References Cited

U.S. PATENT DOCUMENTS

| | | | |
|---|---|---|---|
| 3,691,457 | 9/1972 | Kriellaars | 324/61 R |
| 3,886,447 | 5/1975 | Tanaka | 324/60 CD |
| 4,133,454 | 1/1979 | Arthur | 73/304 C X |
| 4,168,466 | 9/1979 | Boldt | 324/61 R |
| 4,173,892 | 11/1979 | Khurgin | 73/304 C |
| 4,259,865 | 4/1981 | Myers | 73/304 C |

*Primary Examiner*—Stanley T. Krawczewicz
*Assistant Examiner*—Jose M. Solis
*Attorney, Agent, or Firm*—Darby & Darby

[57] ABSTRACT

The invention addresses a new process for determination of characteristic quantities, particularly the moisture content, of a pourable food moving along a product line, particularly grain and its processing products. In this process the good is passed through the electric field of a condenser assembly, a magnitude associable with the capacity of the condenser assembly is measured, and this magnitude is converted into the desired characteristic quantity. The invention further addresses an apparatus to carry out the new process, which includes a first assembly to pass the good through a condenser assembly, a second assembly for measurement of a magnitude associable with the condenser assembly, and a conversion mechanism for conversion of the measured magnitude into the desired characteristic value.

31 Claims, 9 Drawing Figures

METHOD AND APPARATUS FOR THE CONTINUOUS DETERMINATION OF MOISTURE POURABLE FOOD

The invention addresses a process and an apparatus for determination of characteristic values accordable to a pourable food moved along a product path, in particular for grain and its processing products.

In a milling operation, to the present various material characteristics can only be measured with unsatisfactory precision.

The causes for this lie in a large number of factors. The good itself is to be found in two extreme conditions, namely on the one hand at rest, stored in silos, and on the other hand in flow from processing stage to processing stage. It is particularly difficult to obtain exact material values in a continually moving product, and therefore in practice, the laboratory method performed on samples has been used for determination of the exact value. To determine exact material values of a large quantity of a pourable good regularly entails the testing of many samples and the statistical evaluation of the result. Manipulation of the sample taking mechanism is awkward, particularly for large silo cells, since to the extent possible, samples must be drawn from various places within the silo, while within silos very high pressures and compressions are usual.

A further difficulty lies in the fact that the product moisture can vary between relatively wide extreme values, which has a direct influence on the product by volume, and also, for example, the density and electrical conductivity.

In the mill, generally various grain types are mixed together. However, it is not necessary that the mixing of the various sorts be performed very precisely, since in the subsequent processing stages a repeated mixing of the individual fractions can be performed if required. The individual type fractions have various physical properties among them, and in particular the bulk weight is different, and usually the product moisture content as well.

Constrained by these problematics, the measurement by sampling of individual physical quantities has remained an unsolved problem, and this applies quite particularly to the exact determination of the water content in the product.

In a familiar process for determination of the water content in grain, the grain is removed by a mechanism from a product stream in a batch or quasi-continuous operation, and poured in a certain weighed quantity into a measurement container. The measurement container is in part constituted as a condenser, and a measurement is made by determination of an electrical value in the form of the capacitance of the condenser constituted by the container with the product, and in evaluation is converted to the quantity of water present in the sample. This instrument reflects the actual water content of the measurement sample, but it is questionable with this method, whether the measurement values are representative of the entire product stream.

If the product is to be moistened to a particular water content, the product throughput must be received in a subsequent continuously operating weighing system, and the necessary supplemental water quantity computed and added. Although this system is employed relatively frequently in practice, it may often be insufficient for the requirements in a mill. If the moistures or water contents produced are namely determined by an exact laboratory method, for example, in a drying oven, variations in the relative moisture content of frequently up to half a percent, and sometimes up to one percent are discovered. The electrical measurement method here described has the particular failing that the values determined are very much type dependent. To exclude this factor, calibration must be performed for each grain type before beginning measurement. For transparent reasons, this calibration is useless in the case of a mixing of more than one type, if the mixing ratio itself is not precisely known or precisely defined.

It has further been seen that quite a number of measurement methods, for example the exact level measurement of a pourable good, obviously include analogous sources of error.

Grain has particular characteristics in contrast to other products, such as sand. With grain, a living substance is involved, in which water, for example, is present in varied compositions, partly chemically bound, and partly physically. Water is furthermore stored in various zones in grain, and because of life processes in the grain, water is constantly in motion. Alongside the temperature as an important factor, a number of other factors enter as parameters, as for example the season, light and age.

The physical and also electrical behavior of the grain, for example, are subject to constant change, depending on the state of germination.

Appearing especially critical is the question of the water content, with regard to whether the water content has changed soon or long before the measurement. The electrical conductivity is affected by each of the parameters cited.

In milling to the present, in the majority, only the traditional laboratory measurement methods have been given confidence, which, however, has limited a further automation of mills, since such decisive parameters as the exact throughput quantity, the exact moisture content, or even the exact level of the good could not be monitored with sufficient confidence.

A part of the invention is to overcome the known deficiency in the state of the art, in particular to find a new process for determination of physical quantities, in which the values determined for as large as possible a quantity of goods and to as high as possible a precision are made available. The process should render unnecessary any constant recalibration both with respect to special grain types, and with respect to short and long term behavior. The solution is to be simple and economical to manufacture, and be operable even by personnel with little training.

The solution according to the invention is characterized by the fact that the good is passed through the electric field of a condenser arrangement, a quantity associated with the capacity of the condenser arrangement is measured, and this is converted to the characteristic value.

The new conception has proven itself to offer a substantial advancement for the reliability of measurement, particularly in regard to the moisture factor. On the one hand, the new process enables significantly more precise determination of the moisture content of a good, and on the other hand enables exclusion of the moisture content as an interference factor, for example for the exact measurement of throughput or level.

The invention permits various additional, very advantageous refinements. Thus it is particularly advantageous for the capacity to be measured directly.

By preference, the water content of grain and processing products is measured in the manner that at least a portion of the good is passed with slowed motion through a measurement condenser, during which charging measurements are made, and the measurement values are conducted to an evaluation circuit as a base characteristic for determination of the moisture content. In the familiar processes for measurement of physical quantities, it has proven time and again that the detection of the measurement value in the product itself is as difficult to perform as the conversion of the measurement value into a usable signal.

In addition, in the past numerous proposals have been made which, however, in part directly falsify the measurement value, and in part are subject to variation due to long-term influences. The consequences have been false indications, with the corresponding measurement uncertainties; for example, in a mill the miller was forced to constantly recalibrate the instrument. Surprisingly, it has now been found that these problems can be overcome through a very simple procedure, and a very simple measurement process can be conducted. The new, particularly advantageous process is characterized by measurement of the electrical conductivity by detection of the electrical characteristic using a measurement condenser, with the measurement condenser being charged to a given voltage in a first phase, and in a second phase being connected to a reference condenser, passing the charge of the measurement condenser to the reference condenser, and measuring the voltage across the reference condenser, and passing it to the evaluation circuitry. By preference in this process, the two phases are repeated cyclically, with the reference condenser being discharged during the first phase. At the end of the second phase, the voltage across the reference condenser can be passed to a memory. It has further proven advantageous for the cycle to be determined by the power supply frequency. In the memory, a number of measurement values are averaged for determination of the moisture content of the good. If the good to be measured is subject to wide variations in physical characteristics, it is desirable to weigh the good in the measurement condenser, filling the measurement condenser during the measurement to a constant level, or to the top. Very accurate measurement values are obtained when the good continues to flow through the measurement condenser even during the measurement. Very highly reproducible results can be obtained when the measurement condenser is supplied by a continuous flow of the good, and a substream is diverted by the overflow principle to a parallel bypass conduit, with the two substreams being reunified afterward, producing in the region of the reuniting of the two substreams a backwash of product onto the measurement condenser.

In this conception, it is a goal for the movement of good in the bypass path to be controlled in such a way that the level of good in the bypass path remains constant, to ensure a constant backwash of good on the measurement condenser.

A conception for refinement of the invention for determination of characteristic quantities to be accorded to a pourable food moving along a product line, in particular for grain and its processing products, lies in passing the good through the electric field of two condenser assemblies, one over the other, and obtaining a charging measurement of both condenser assemblies, the passing the measurement values to an evaluation circuit as a basis characteristic for determination of the level of the good. This conception can be applied especially advantageously for determination of the good level in the product supply path of a milling roller carriage, then using a feed control gate to control the product stream to a constant level.

The invention relates further to an apparatus especially for the performance of the process described above for measurement of characteristic quantities to be accorded to pourable food moving along a product line, particularly for grain and its processing products, and characterized by a first assembly for conducting the good through a condenser arrangement, a second assembly for measurement of a magnitude accordable to the condenser arrangement, and a converter assembly for conversion of the measured magnitude to the characteristic quantity. By preference, the condenser assembly takes the form of a measurement container and a pass-through container. The container wall can assume the function of one condenser plate, and a second condenser plate can be arranged within the container. To prevent disturbing influences due to large temperature variations, it is desirable for a pourable good temperature sensor to be positioned in the vicinity of the container. A bypass duct is arranged parallel to the measurement container, along with a regulator mechanism for control of the movement of the good in the measurement container and in the bypass path.

Investigations have shown further that both the measurement method and the constructional configuration of the measurement path, i.e. the product pathway, have similar influence on the measurement precision. Very good results could be obtained when the first assembly for feed of the good has a product inlet and product outlet, with the product inlet opening essentially vertically above the measurement container, and having a transfer channel to the bypass duct. Associated with the measurement path, there can be at the product outlet a throughput control mechanism, controlled by a level senser included in the control mechanism. It has been found to be very advantageous for the level senser to take the form of a membrane placed laterally in the control channel, which advantageously actuates the throughput control mechanism by pneumatic means. Since the configuration described above includes automatic flow, for practical application it is desirable to provide manual apparatus for opening and closing of the throughput control mechanism. In order for the apparatus to be applicable for automatic regulation and control, preferably a throughput quantity measurement device is placed after the measurement path, to determine the instantaneous throughput. In the evaluation circuit, the quantity of water to be added can be determined by means of a second computer and a moisture content target value input.

The invention for the first time permits fully automatic regulation and control of moisture content and water addition for grain and its processing products, such as flour and grits, in that the evaluation circuitry is directly connected to a wetting apparatus having a regulable water addition mechanism, with the water addition being made between the mechanism and the wetting apparatus, and the wetting apparatus has a closed housing with a rapidly turning intensive wetting rotor, whereby the water content is regulated in a open or direct control loop, on the basis of the instantaneous throughput quantity.

In a particularly advantageous variation, in which the pourable good is drawn directly from a silo or intermediate storage container, the pourable good measurement path has at the product outlet a throughput measurement and control mechanism controlled by a corresponding target value regulator in the evaluation circuitry. The pourable good measurement pathway in this way has a dual function, namely moisture content determination, as well as precise throughput quantity measurement, with the pourable good measurement section being placed directly below a storage container, and the throughput measurement and control mechanism regulating the outlet quantity from the storage container. If a second computer is accorded to the evaluation circuitry, a subsequent apparatus can be controlled, such as a wetting or drying mechanism.

A further interesting refinement conception lies in configuring the condenser mechanism as a weighing container, with the weighing signal being passed to the evaluation circuitry, wherein the condenser mechanism includes a plate, scattering field or cylinder condenser.

The invention will now be described in greater detail by reference to a number of examples of realization. The figures show.

Figure 1:
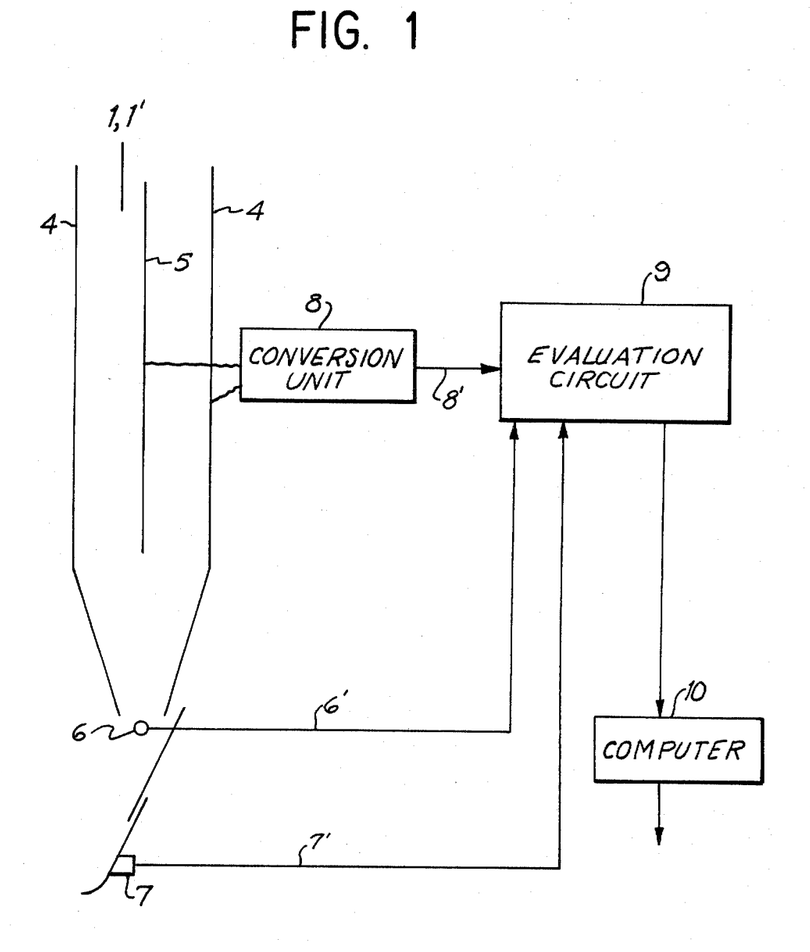
in FIG. 1, a conceptual representation of the invention.

FIG. 1 shows a conceptual representation of the apparatus. A measurement container 1 is a component of a pourable good measurement section 1'. The measurement container 1 takes the form of a condenser, in which a wall of the measurement container 1 is configured as a condenser plate 4, and a second condenser plate 5 is placed within the container. Below the measurement container 1 is placed a pourable good temperature sensor 6. Below the outlet of the pourable good measurement section 1' is a throughput quantity measurement instrument 7. The measurement values are processed to obtain the desired characteristic quantities partly in a conversion unit 8, and in an evaluation circuit 9.

The solution represented in FIG. 1 is the conceptual foundation for the measurement of the moisture content of grain, and, supplemented with the cited throughput quantity measuring instrument 7 and a second computer 10, can be used directly to control the wetting of the grain to a particular value.

Figure 2:
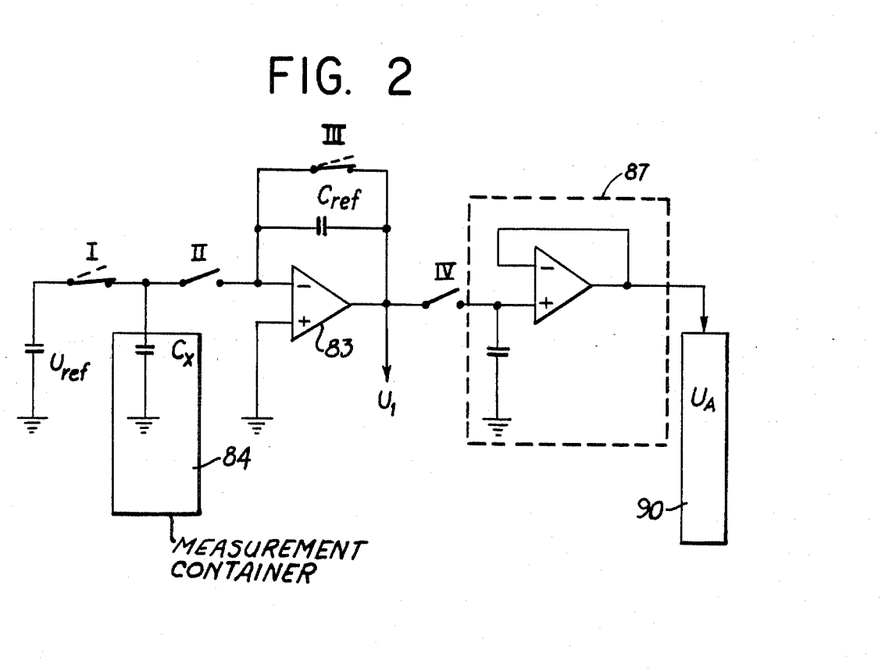
in FIG. 2, a symbolic representation of the measurement process.

In FIG. 2 is a conceptual representation of the new measurement process. In a measurement container 84 configured as a condenser, analogous to the measurement container 1 of FIG. 1, the capacitance is measured.

Figure 3:
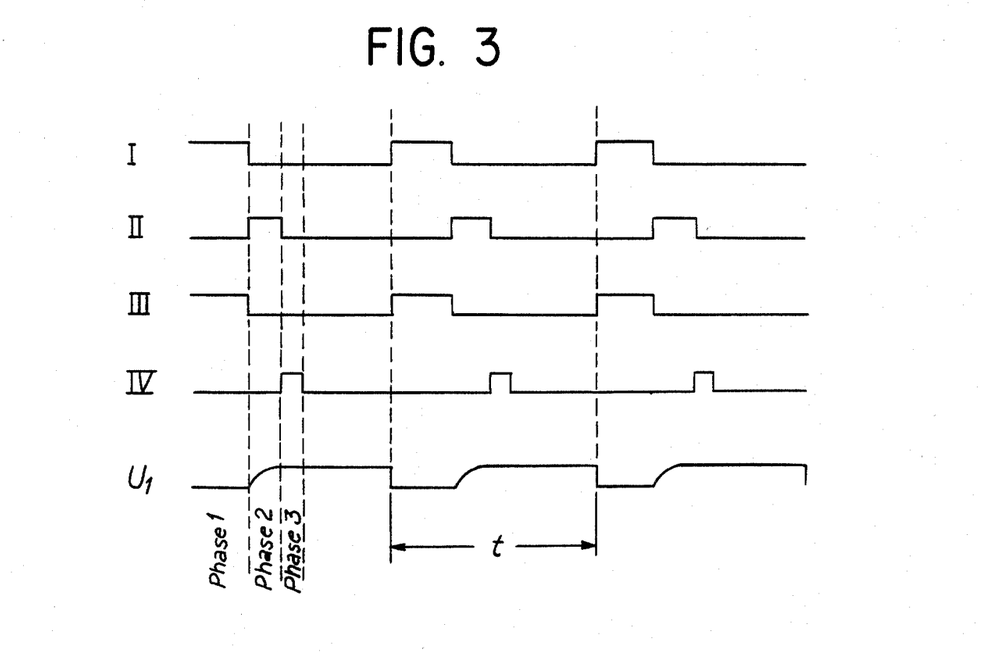
in FIG. 3, the positioning of individual switches in time sequence.
Figure 4:
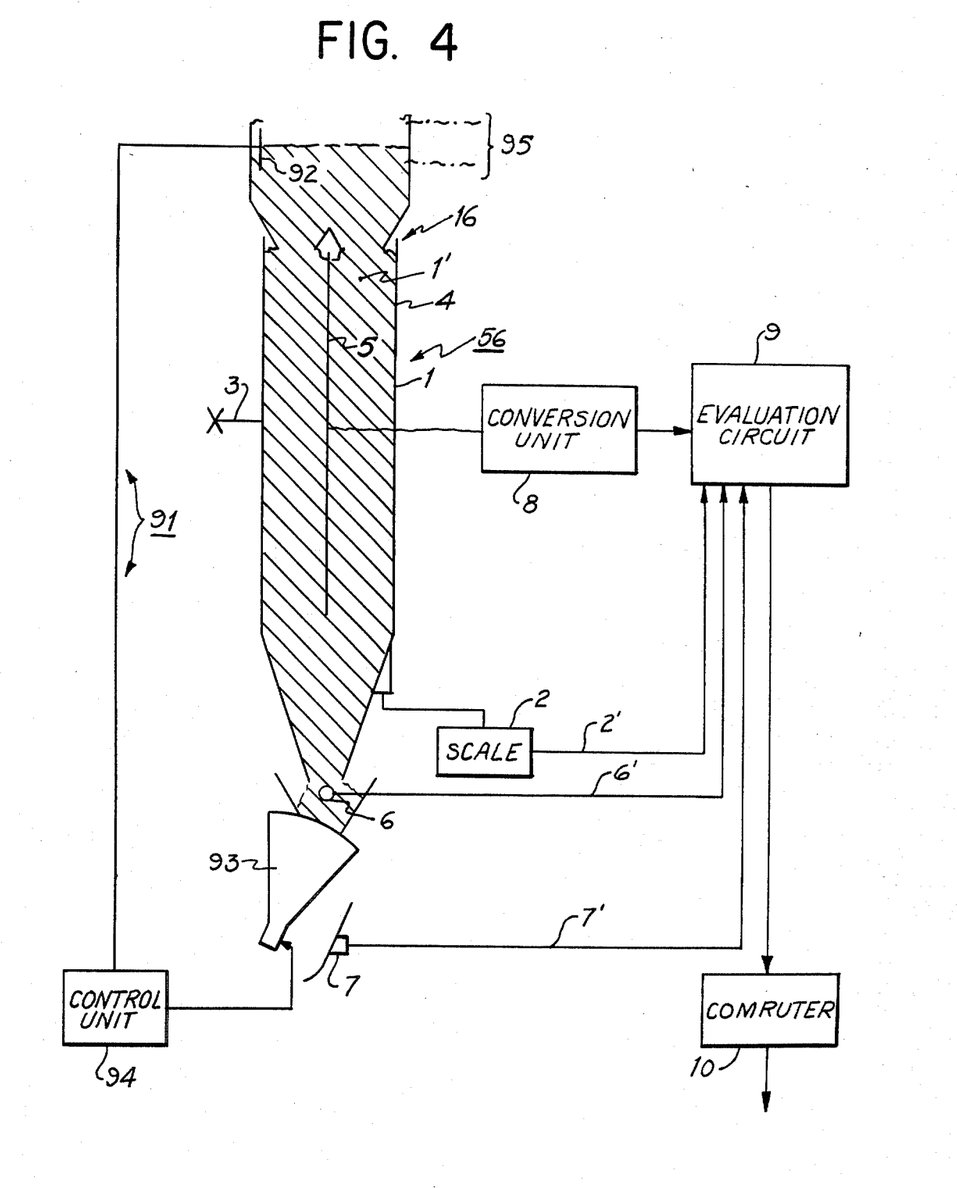
in FIG. 4, the measurement of moisture content and control of throughput rate by the measurement section.

For the description of the performance of the measurement, reference will made at the same time to FIGS. 3 and 4 as well.

FIG. 3 shows the individual switch positions of the switches I-IV in FIG. 2 during the measurement, and the trace of the voltage $U_1$.

In an initial phase, the measurement condenser $C_x$ is charged to a particular voltage $U_{ref}$. At the same time, the reference condenser $C_{ref}$ is discharged. Switches I and III are closed. Switches II and IV are spaced (position as in FIG. 2). The voltage $U_1$ is still zero in the initial phase. In the second phase, the charge of the measurement condenser $C_x$ is transferred to the reference condenser $C_{ref}$. The switch II is closed for this purpose, and the switches I, III and IV are opened. The voltage $U_1$ rises until the measurement condenser is fully discharged. This charge transfer is effected by means of the operational amplifier 83. In a third phase, the voltage of $U_1$ is transferred to an analog memory 87. For this purpose, the switch IV is closed, and the switches I-III opened. This phased charging and discharging of the measurement and reference condensers $C_x$ and $C_{ref}$ is controlled by preference by the cycle of the power supply frequency.

FIG. 4 shows a particularly advantageous example of realization built on the basic elements of FIGS. 1, 2 and 3. The corresponding parts are therefore labelled with the same reference numbers. In FIG. 4, there is in addition a control mechanism 91 to control the sinking movement of the good in the measurement section 1' or in the measurement container 1. The control mechanism 91 includes a level sensor 92 and an adjusting gate 93. The signals from the level sensor 92 are processed by a control unit 94.

The purpose of the control mechanism 91 is for the product to be passed with retardation through the measurement section 1' or the measurement container 1. The solution in FIG. 4 can be employed in such a way that the entire goods stream is passed through the measurement section 1'. The total throughput quantity through the measurement section need not be changed in this application. The control mechanism 91 serves merely to impede the product movement to a greater or lesser extent, so that the measurement container 1 is constantly filled with the good. To ensure filling, by means of the control mechanism 91, through regulation of the opening of the adjusting gate 93, the level of the good is maintained within a constant range 95.

Through means not represented, it can be ensured that the extreme positions without product and without further feed of product, or the closed position of the adjusting gate 93 resulting in possible false indications or false commands from the evaluation circuitry are avoided.

FIG. 4 shows the further possibility of the determination of the weight of the good by a weighing mechanism, consisting of a pressure sensor or scale 2 and a corresponding support pivot 3. In this example, the measurement container 1 is simultaneously configured as a weighing container. The weighing container can be used both as a continuous throughput scale, or as a batch scale, depending on the position of the adjusting gate 93.

It has been found that in the case of extreme product variations, particularly with regard to electrical conductivity, the additional weighing, and evaluation of the weight measurement, advantageously determined simultaneously with the electrical measurement, yields an increased level of confidence for the measurement result. Interestingly, however, it has been found that in many applications, very good representative values are obtained even without weight or pouring density measurement.

The evaluation circuitry can in addition be programmed in such a way that the weight is constantly measured, for example, but is not taken into account in the evaluation as long as it lies within the range of the known acceptable limits. This solution can be valuable, for example, if the moisture content of raw wheat is being measured normally. If, for example, the wheat has been insufficiently cleaned, or if a high degree of separation has occurred in the foregoing silo compartment, so that the last material leaving it consists more of dust and dirt etc. than of wheat, in this case due to the large proportion of husks and mineral components, the indicated characteristic values, such as the moisture content, will be false.

Taking the density into account can on the one hand be used as a confidence factor, or, on the other hand, in the case of actual large variations in the density, can be used for correction of the measurement value.

Figure 5:
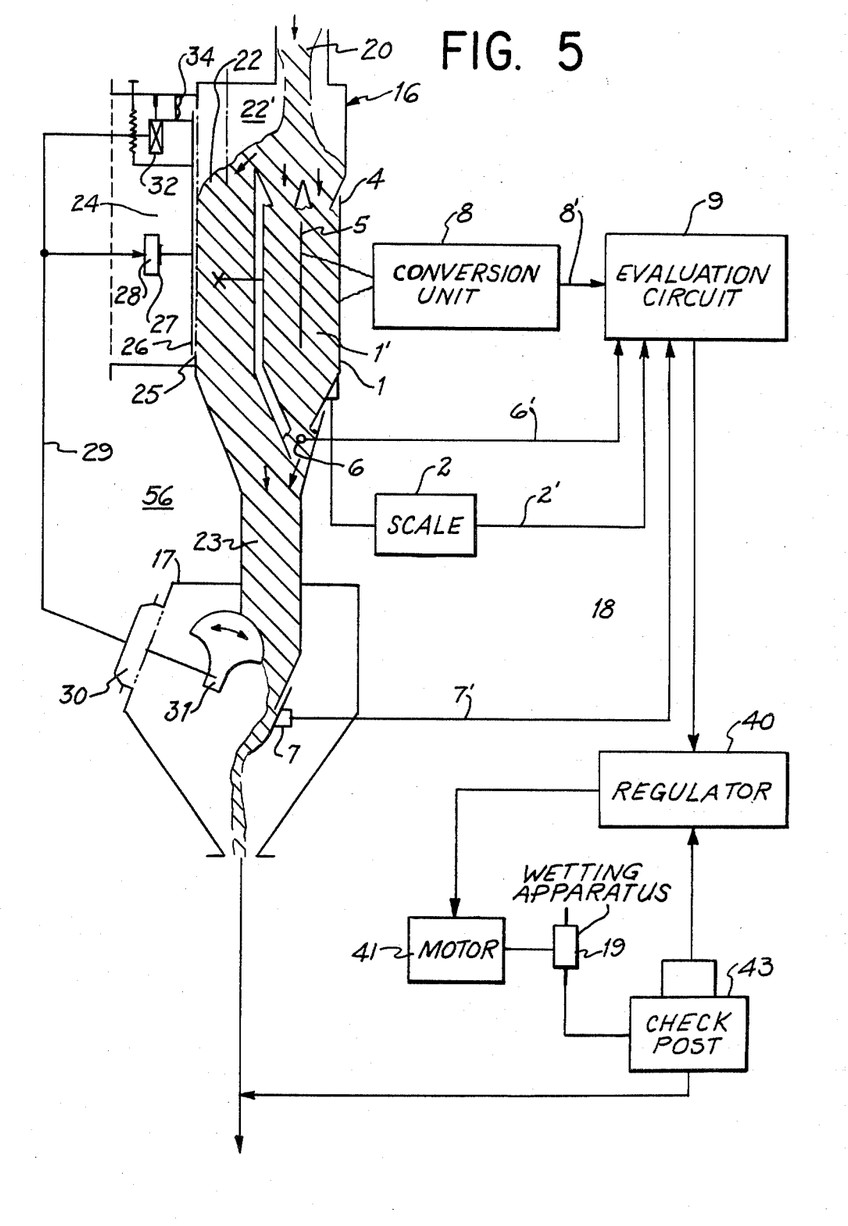
in FIG. 5, a conceptual schematic for the control and regulation of a grain wetting mechanism.

In FIG. 5 is represented an application of the invention for measurement and control of the water content of a pourable good. The apparatus displays a measurement container 1 with a throughput regulating mechanism 17, and a regulation and control loop 18, which includes an evaluation circuit 9 and a wetting apparatus 19. Components the same as those in FIGS. 1 and 4 are given the same reference numbers.

The measurement section 16 has an inlet 20, opening essentially vertically above the measurement container 1. Parallel to the measurement container 1 runs a regulating channel 22. The regulating channel 22 and the measurement container 1 flow together in the region above the product outlet 23. The product outlet 23 is controlled by means of a throughput regulating mechanism 17, in which a level detector 24 is included in the form of a membrane 25 in the side of the regulating channel 22.

A strut 26 is pivoted on a joint 34, and a pneumatic regulator valve 32 is connected with the strut 26. At a certain pressure of the product, through the membrane 25 and the strut 26, the pneumatic regulator valve 32 is actuated, producing an air pressure in a duct 29. This air pressure operates a pressure cylinder 30, which in turn controls the gate 31 at the product outlet 23. The same pressure present in the duct 29 also enters a pressure chamber 28 and acts on a membrane 27. Here the pressure serves as a compensating pressure against the product pressure.

In the regulating channel 22 are also manual actuating means for the opening and closing of the throughput regulating mechanism 17. A screw 33 and the strut 26 permit actuation of the pneumatic regulator valve 32, and thus completely open or close the gate 31. With this manual actuation mechanism, it is possible to fully empty the pourable good measurement section 1, for example to perform testing of the measurement condenser.

Below the product outlet 23 of the measurement container 1 is placed a throughput quantity measurement instrument 7, which establishes the instantaneous throughput quantity. Thus with the measurement values of the condenser, of the pourable good temperature sensor 6, the scale 2 and the throughput quantity measurement instrument 7, a moisture deficiency value can be determined. In the evaluation circuit 9, the moisture deficiency value is passed as a control quantity to a regulator 40, which controls a motor 41 which conveys the computed quantity of water lacking into the product stream. As a control, the water quality delivered is echoed by a check post 43.

Figure 6:
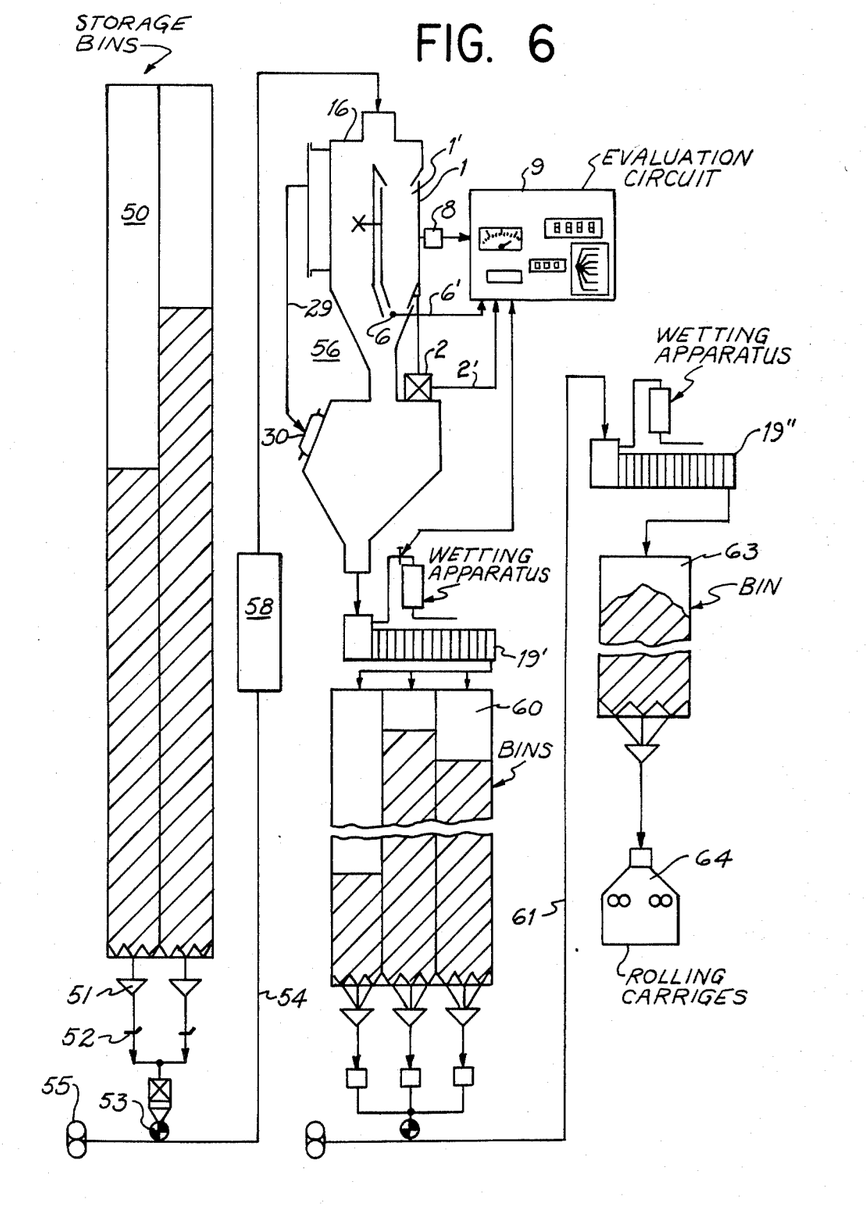
in FIG. 6, the use of the solution according to FIG. 7 in a mill.

In FIG. 6, the components the same as those in FIG. 5 are given the same reference numbers. FIG. 6 shows the basic plan of an installation with the new measurement apparatus.

The raw product is drawn from storage bins 50 through special outlets 51, which hinder separation, an approximate outlet rate is established by means of a gate 52, and is fed through a bucket wheel sluice 53 and a pneumatic barrow train 54 supplied with air from the blower 55, into the moisture measurement apparatus 56.

The details of construction of the measurement container 1 are represented in FIG. 5. The wetting apparatus 57 in the preferred solution has a closed housing with a rapidly turning intensive wetting rotor. The water content of the grain is determined in the measurement container 1, and regulated in an open or direct control loop by means of the evaluation circuit 9 and the wetting apparatus 57.

The wetted grain is conveyed into standing bins 60. Depending on the wheat variety and the desired flour products, the grain can be removed from the standing bins 60 after an appropriate number of hours, to be conveyed through another pneumatic transport 61 into an intensive wetting apparatus 62, where a small additional quantity of water is added. Usually here a few tenths of a percent of water is applied as a water film on the grain, and after a working period in standing bins 63, the grain is transferred directly to the rolling carriages 64.

Figure 7:
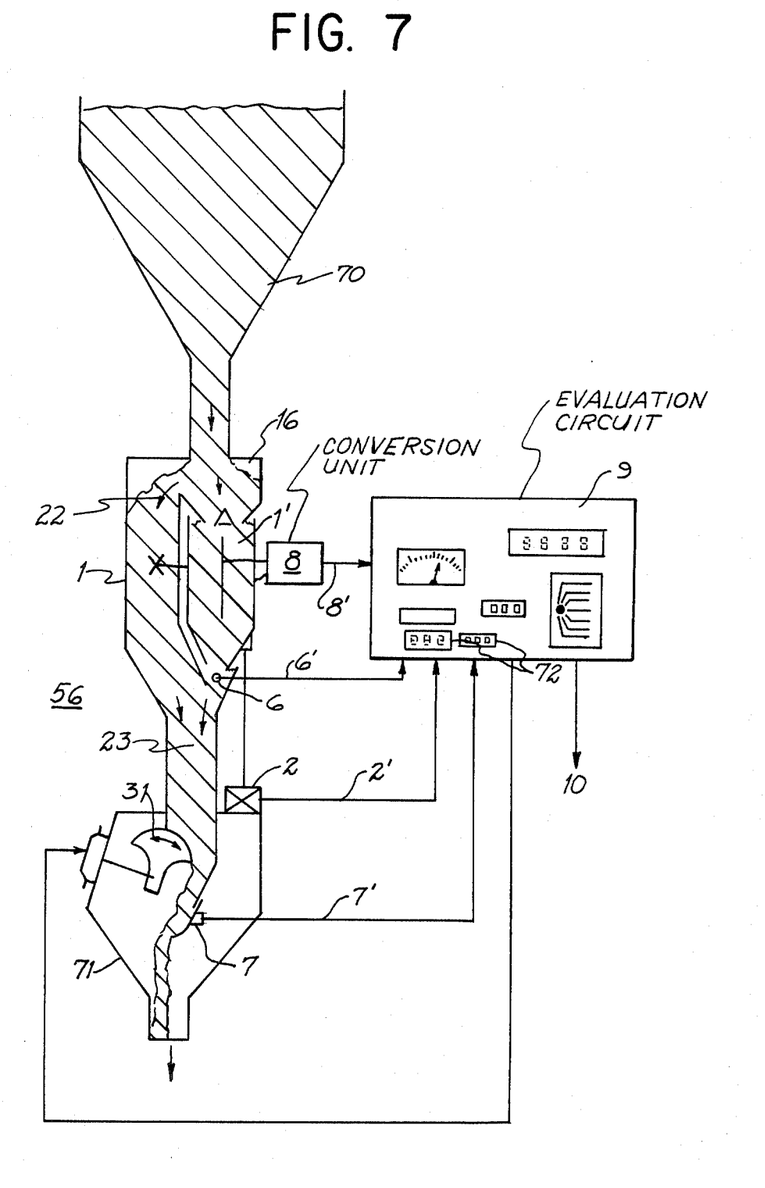
in FIG. 7, the measurement of the moisture content and throughput quantity directly in the product stream from a silo.

FIG. 7 shows the apparatus installed directly below a silo. Identical parts to those of FIG. 5 are given the same reference numbers.

The product flows from a silo container 70 directly through a measurement section 16, which is subdivided into a measurement container 1 and a regulating channel 22. At the product outlet 23 is a throughput measurement and control mechanism 71, controlled by an appropriate target value regulator 72 in the evaluation circuit 9. The throughput measurement and control mechanism 71 consists of a throughput quantity measurement instrument 7, and a regulable gate 31. In the evaluation circuit 9, the water content and throughput are combined, and a wetting or drying process, not represented, is controlled by a control signal 10.

The apparatus according to the invention, in the application represented, receives a double function, on the one hand to determine the precise moisture content of the pourable good, and on the other hand to achieve an exact outlet quantity from the silo container.

Figure 8:
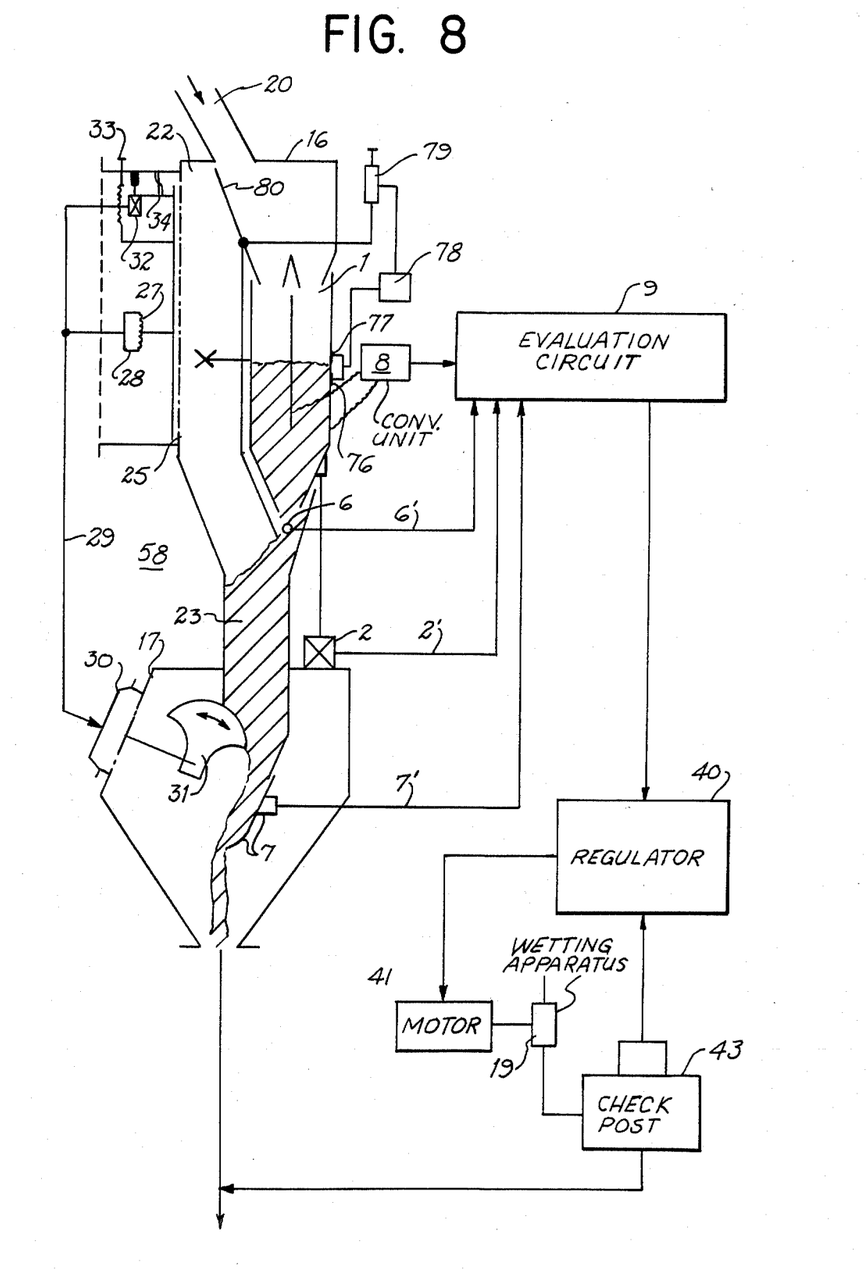
in FIG. 8, a variant of FIG. 5.

In FIG. 8, a constructional configuration of the measurement apparatus is represented. The same parts as in FIG. 5 are given the same reference numbers.

The inlet 20 feeds above the regulating channel 22 and the measurement container 1 essentially obliquely into the measurement container 1. At the side of the measurement container 1 is placed a pourable good level sensor 75. This apparatus includes two measurement detectors 76 and 77, an evaluation and control circuit 78 and 79, and a trap 80.

The pourable good level in the pourable good measurement section 1 is regulated to a particular height, in that the two measurement detectors 76 and 77 give appropriate signals to the evaluation circuit 78. If both measurement detectors 76 and 77 detect the presence of product, through the evaluation circuit 78 and the control circuit 79, the trap 80 is positioned on that the product flows into the regulating channel 22; if only the lower detector, or in exceptional cases neither detector, indicates the presence of product, through the evaluation circuit 78 and the control circuit 79, the trap 80 is positioned so that the product flows into the pourable good measurement section 1.

The water content measurement and regulation occur just as described in FIG. 5.

Figure 9:
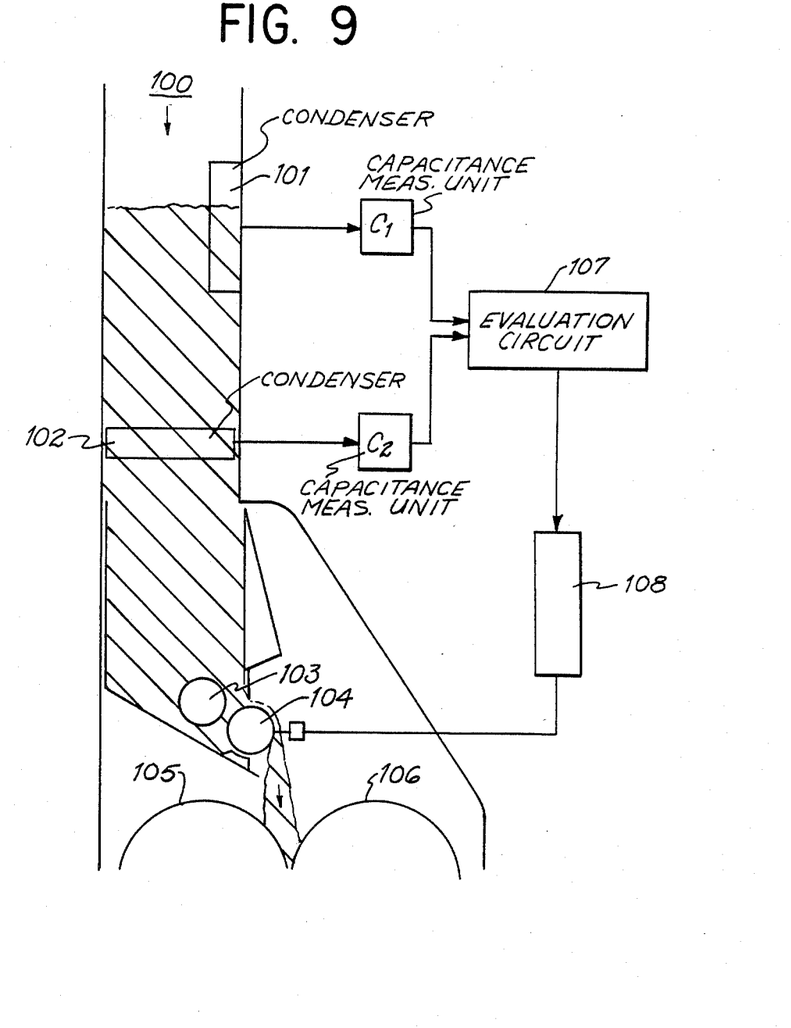
in FIG. 9, measurement and regulation of the level in a mill rolling carriage.

FIG. 9 shows the application of the new measurement method for level regulation or control in the inlet to a milling roller carriage. In the feed line 100 is placed a first condenser 101, of which the capacity $C_1$ is measured, followed by a second condensor 102, of which the capacity $C_2$ is measured. The good flows through a distributing roller 103 and dosing roller 104 to the actual milling rollers 105 and 106. In the evaluation circuit 107, a quotient is formed of the measured capacities $C_1$ and $C_2$, and the characteristic value obtained, in this case the level of good, is used to control the dosing roller 104. As soon as the lower condenser is not at all, or only partially, covered by product, or both condensers 101 and 102 are completely uncovered, an electrical signal from the evaluation circuit commands the separation of the milling rollers. For measurement of the capacities $C_1$ and $C_2$, the circuit of FIGS. 2 and 3 is used, whereby in the normal case the level of good is regulated within the electric field of condenser 101 by means of the dosing roller 104. A further application of the new capacitance measurement is for level measurement in dosing containers. In the vicinity of the outlet of the dosing container is placed a first condenser, and somewhat above it a second condenser. Obviously the apparatus can also be further refined, for example by using an analog signal directly for gradually increasing a feed rate. In this case, it is desirable to measure the capacity 101 over a substantial height, for example 10 to 50 cm.

We claim:

1. A process for achieving measurement of the water content of moisture of a pourable food product stream moved along a production path, comprising the steps of passing the product continuously through an electric field created between conducting surfaces defining a condenser apparatus, measuring a quantity related to the capacitance of the condenser apparatus, converting the quantity to a characteristic value signal representing the product level, passing at least a part of the product through a measurement condenser with retarded motion, during which the measurement condenser is electrically charged in accordance with a predefined procedure, the amount of resultant charge stored on the condenser defining measurement values, passing the measurement values to an electronic evaluation circuit for determination of the moisture, and controlling the motion of said product to maintain said characteristic value substantially constant, whereby said condenser is filled to a predetermined level as the product passes through the measurement condenser during said moisture determination.

2. Process according to claim 1, characterized in that the measurement condenser is charged to a particular voltage in a first phase, and in a second phase a reference condenser of known capacitance is connected to the measurement condenser, charge of the measurement condenser is transferred to the reference condenser, and the voltage is measured across the reference condenser, and passed to the evaluation circuitry.

3. Process according to claim 2, characterized in that the two phases are repeated cyclically.

4. Process according to claim 3, characterized in that during the first phase the reference condenser is discharged.

5. Process according to claim 3, characterized in that the cycle repetition rate is determined by the power supply frequency.

6. Process according to claim 2, characterized in that at the end of the second phase, the voltage across the reference condenser is passed to a memory.

7. Process according to claim 6, characterized in that in the memory, a number of measurement values are averaged, and used for determination of the moisture of the product.

8. Process according to claim 1, characterized in that the measurement condenser is operated in a continuous throughput process.

9. Process according to claim 1 characterized in that the product is passed through the electric fields of two condenser arrangements spaced along the product flow path, a charging measurement of both condenser arrangements is obtained, and the measurement values passed as a basis characteristic to an evaluation circuit, for determination of the level of the product.

10. Processes according to claim 9, characterized in that the product level in the product supply line of a milling roller carriage is determined, and controlled to a constant height range by a feed regulation gate.

11. A process for generating a characteristic value signal representing the level of a pourable food product stream moved along a production path, comprising the steps of passing the product continuously through an electric field created between conducting surfaces defining a condenser apparatus, measuring a quantity related to the capacitance of the condenser apparatus, converting the quantity of the characteristic value, passing at least a part of the product through a measurement condenser with retarded motion, during which the condenser is electrically charged in accordance with a predefined procedure, the amount of resultant charge stored on the condenser defining measurement values passing the measurement values to an electronic evaluation circuit for determination of the moisture, the product being weighed while retarded in the measurement condenser, and during the measurement filling the condenser to a predetermined level.

12. A process according to either claim 1 or 11 characterized in that the capacitance of the condenser apparatus is measured by electrically activating the condenser and directly measuring its electrical state.

13. Process according to claim 11, characterized in that the measurement condenser is integral with a compartment through which the product flows, the compartment being filled essentially to its capacity with the product for the measurement.

14. A process for generating a characteristic value signal representing at least one of the level and the height of a pourable food product stream moved along a proportion path, comprising the steps of passing the product continuously through an electric field created between conducting surfaces defining a condenser apparatus, measuring a quantity related to the capacitance of the condenser apparatus, and converting the quantity to the characteristic value, the capacitance being measured by electrically activating the condenser and directly measuring its electrical state, supplying the measurement condenser with a continuous product stream, and diverting a partial stream by an overflow principle into a parallel bypass path defined by a bypass channel of predetermined dimensions, and reuniting the two substreams later.

15. Process according to claim 14, characterized in that in the region of the reuniting of the two substreams, a backward accumulation of product to the measurement condenser is produced.

16. Process according to claim 14, characterized in that the flow of product in the bypass path is controlled to attain a constant level in the bypass path, to assure a constant backward accumulation on the measurement condenser.

17. Apparatus for generating a characteristic value signal representing the level of a pourable food product stream moving along a product path, comprising: condenser means constructed to have said product pass continuously therethrough, means for passing the product through said condenser means, means for measuring an electrical property of said condenser means, and converter means for converting the measured value into the characteristic value signal, the condenser means being supported on pressure measurement means for producing a weighing signal proportional to the quantity of product within the condenser means, the weighing signal going to the evaluation circuit.

18. Apparatus for generating a characteristic value signal representing the level of a pourable food product stream moving along a product path, comprising condenser means in the form of a measurement container constructed to have said product pass continuously therethrough, means for passing the product through said condenser means, means for measuring an electrical property of said condenser means, and converter means for converting the measured value into the characteristic value signal, further comprising a bypass channel of predetermined dimensions adjacent the measurement container and control means for controlling the movement of the product in the measurement container and in the bypass channel.

19. Apparatus according to claim 18, characterized in that the condenser means has a product inlet and product outlet for passage of the product the product inlet being positioned substantially vertically above the measurement container, said apparatus further comprising a transfer channel to the bypass channel.

20. Apparatus according to claim 18, characterized in that the measurement container takes the form of a pass-through container.

21. Apparatus according to claim 18, characterized in that the container includes a wall defining a condenser plate, and a second condenser plate is placed within the measurement container.

22. Apparatus according to claim 18, characterized in that it has a pourable product temperature sensor.

23. Apparatus according to claim 18, characterized in that the condenser arrangement includes one of: a plate, stray field, or cylinder condenser.

24. Apparatus according to claim 18, characterized in that it has two condenser means each one positioned at a different height for measurement of the product level.

25. Apparatus according to claim 19, characterized in that it has a throughput control gate at the product outlet, and a level detector placed in the bypass channel are coupled to control said gate.

26. Apparatus according to claim 25, characterized in that the level detector comprises a membrane placed lateraily in the bypass channel, which is connected with the throughput control gate.

27. Apparatus according to claims 25 or 26, further comprising manual actuating mechanisms for opening and closing the throughput control gate.

28. Apparatus according to claim 18 further comprising throughput volume metering means which measures the instantaneous throughput.

29. Apparatus according to claim 18 further comprising a throughput control gate, and throughput volume metering means and desired value regulator means in an evaluation circuit connected to control at least one of said gate and said metering means.

30. Apparatus according to claim 29, in combination with a storage container and placed directly below said storage container in such a way that the outlet volume from the storage container can be controlled by the apparatus.

31. Apparatus according to claim 30, characterized in that the evaluation circuit includes a second computer for control of a subsequent processor.

* * * * *